United States Patent [19]

Wiley

[11] 4,318,790

[45] Mar. 9, 1982

[54] PHOTOCHEMICAL PROCESS FOR PREPARING N-DEMETHYL-DERIVATIVES OF NOGALAMYCIN

[75] Inventor: Paul F. Wiley, Portage, Mich.

[73] Assignee: The Upjohn Company, Kalamazoo, Mich.

[21] Appl. No.: 130,894

[22] Filed: Mar. 17, 1980

[51] Int. Cl.³ .............................................. B01J 19/12
[52] U.S. Cl. ................................................. 204/158 R
[58] Field of Search ............ 204/158 R, 158 N, 158 T

[56] References Cited

U.S. PATENT DOCUMENTS 4,064,340  12/1977  Wiley et al. .......................... 536/17
4,086,245  4/1978  Wiley et al. ...................... 260/340.3

*Primary Examiner*—Howard S. Williams
*Attorney, Agent, or Firm*—Sidney B. Williams, Jr.

[57] ABSTRACT

Photochemical process for preparing N-demethyl-derivatives of nogalamycin.

9 Claims, No Drawings

PHOTOCHEMICAL PROCESS FOR PREPARING N-DEMETHYL-DERIVATIVES OF NOGALAMYCIN

The invention described herein was made in the course of, or under U.S.P.H.S. Grant No. N01-CM-77100 with the National Cancer Institute, National Institutes of Health, Bethesda, Md. 20014.

DESCRIPTION

BACKGROUND OF THE INVENTION

The antibiotic nogalamycin, and a process for its preparation, are described in U.S. Pat. No. 3,183,157. The structure of nogalamycin can be shown as follows:

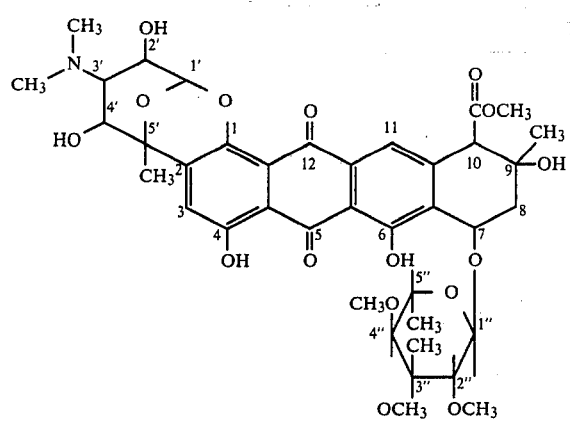

Antibiotics nogalarol and nogalarene, produced by acid hydrolysis of nogalamycin, and O-methylnogalarol, produced by acidic methanolysis of nogalamycin or nogalarol, are disclosed in U.S. Pat. No. 3,501,569.

Nogalamycinic acid is prepared by chemical modification of nogalamycin as disclosed in U.S. Pat. No. 4,064,341. The structure of nogalamycinic acid is as follows:

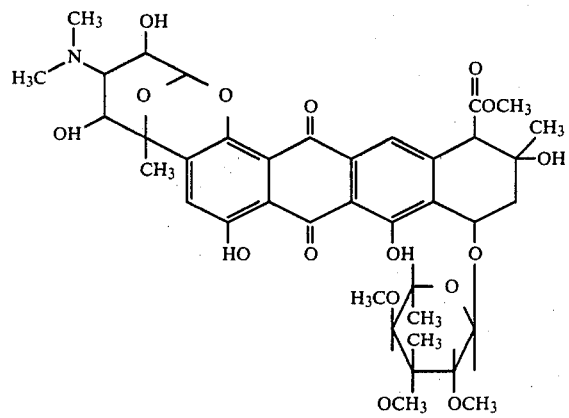

Nogalamycinic acid can be converted to nogamycin by contacting it with dimethylformamide (see U.S. Pat. No. 4,064,340). Nogamycin has the following structural formula:

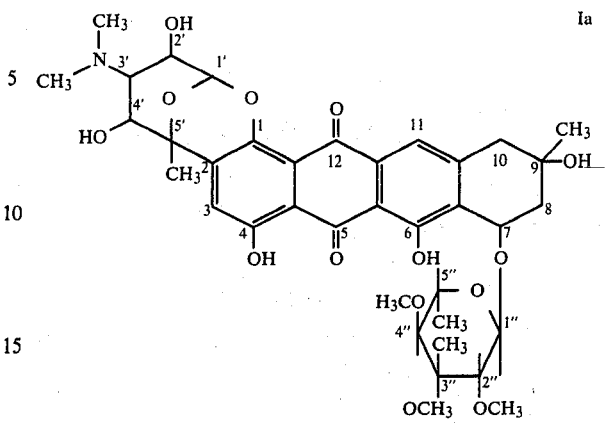

It is now found that the nogamycin prepared in the process of the above citation is dis-nogamycin. In dis-nogamycin and its analogs, the 9-hydroxy and 7-substituents are on opposite sides of the ring system.

U.S. Pat. No. 4,086,245 and U.S. application Ser. No. 924,975, now U.S. Pat. No. 4,183,860 concerns 7-O-alkylnogarols and their preparation from nogamycin.

Acid alcoholysis of nogamycins is the process used in the above preparations of 7-O-alkylnogarols having the following formulas:

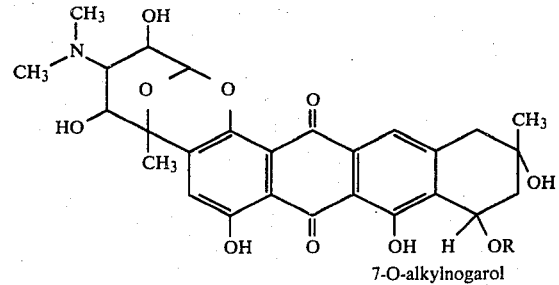

7-O-alkylnogarol wherein R is an alkyl group of from 1 to 4 carbon atoms, inclusive.

Additional prior art includes disclosure by Tong et al.; in Abstracts of Papers, 175th ACS meeting. Medicinal Division, paper 48, for a process which treats daunomycinone with 2-aminoethanethiol in trifluoroacetic acid solution to obtain two diastereomers of a 7-(2-aminoethylthio) derivative.

Demonstrated advantageous biological use for the 7-O-alkylnogarols are included in U.S. Pat. No. 4,086,245 and copending U.S. Ser. No. 924,975. Nogamycin itself has a demonstrated advantageous use in U.S. Pat. No. 4,064,340.

Applicants pending U.S. application Ser. No. 060,326 filed July 25, 1979, now abandoned describes structurally novel nogamycin, 7-nogarols and 7-deoxynogarols having the formula:

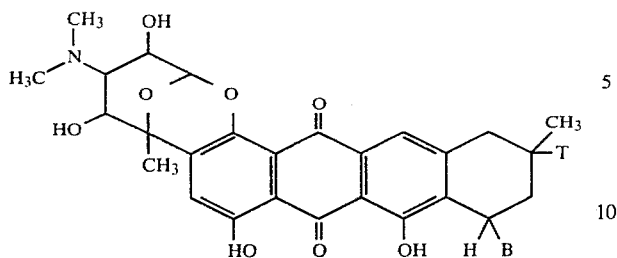

wherein B is a nucleophile from a group comprising nogalosyl, a sulfide anion, organic acid anion, amino, substituted amino and carbanion, with the proviso that B is not -O-lower alkyl and T is hydroxyl such that B and T are attached to the ring system of I in the con configuration. Con compounds are defined as those in which the 9-hydroxy and 7-B substituents are either both above or below the ring system.

BRIEF SUMMARY OF THE INVENTION

Novel con and dis-N-demethyl derivatives of nogalamycin, are prepared by subjecting the corresponding N-dimethyl compounds to photolysis.

DETAILED DESCRIPTION OF THE INVENTION

The compounds of this invention have the formula:

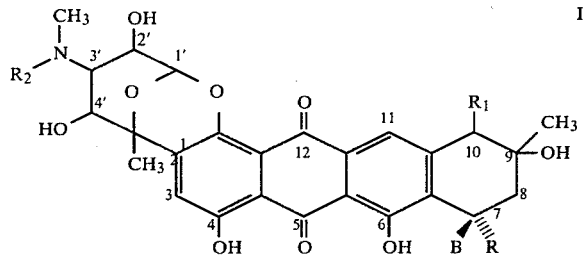

wherein R is selected from the group consisting of hydrogen and nogalosyl; $R_1$ is selected from the group consisting of hydrogen, carboxy and carbomethoxy; $R_2$ is selected from the group consisting of acyl and hydrogen; and B is selected from the group consisting of hydrogen and a nucleophile; acylates thereof; biologically acceptable acid addition salts of said compounds wherein $R_1$ is hydrogen or carbomethoxy and $R_2$ is hydrogen; and non-toxic alkali metal and alkaline earth metal salts of said compound wherein $R_1$ is carboxy and $R_2$ is hydrogen.

Nucleophile is meant to be non-limiting and subgenera named herein are only suggestions from a broad range of possible reacting groups known in the art to react because of the presence thereon of an unshared pair of electrons. In addition to specific groups such as alkylthioxy, acyloxy, bis(carbalkoxy)methylaminoalkylalkoxy, and alkoxyalkylamino, comprising B above, it is suggested that B also comprises alkoxy, aryloxy, aralkoxy, and the corresponding sulfoxy groups, as well as nitrogen moieties having the formula:

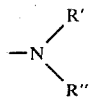

The symbol

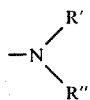

comprises an N-substituted heterocyclic group wherein R' and R" taken together with the nitrogen form the heterocyclic group such that R' and R" have up to two heteroatoms selected from the group consisting of nitrogen, sulfur and oxygen and wherein the heterocyclic group is a group having up to 7 carbon atoms.

The symbol

also comprises an amino group wherein R' and R" selected from the group consisting of H, alkyl, alkenyl, cycloalkyl, cycloalkenyl, cycloalkalkyl, cycloalkenylalkyl, aryl, aralkyl, aralkenyl, aryloxyalkyl, heterocyclic, or heterocycloalkyl, wherein the heteroatoms are nitrogen, oxygen or sulfur having up to 10 carbon atoms apart from any substituents attached thereto, of which there may be one or two selected from hydroxy, carboxy, amino, lower alkoxy, benzyloxy, halogen, or lower alkyl.

When used herein the terms alkenyl are intended to include those containing up to four carbons such as ethylene, propylene, butylene and isomers thereof.

With respect to the alkylthioxy referred to above, there are included methylthioxy, ethylthioxy, n-propylthioxy, isopropylthioxy, n-butylthioxy, isobutylthioxy, and tertiarybutylthioxy moieties.

Acyloxy means acetoxy, n-propionyloxy, isopropionyloxy, n-butyryloxy, isobutyryloxy and tertiarybutyryloxy.

Bis(carbalkoxy)methyl means bis(carbomethoxy)methyl, bis(carbethoxy)methyl, bis(carbo-n-propoxy)methyl, bis(carboisopropoxy)methyl, bis(carbo-n-butoxy)methyl, bis(carboisobutoxy)methyl and bis(carbotertiarybutoxy)methyl.

Aminoalkylalkoxy means aminomethylmethoxy, aminoethylmethoxy, aminopropylmethoxy, aminobutylmethoxy, and isomers thereof.

Alkylamino means methylamino, dimethylamino, ethylamino, diethylamino, propylamino, butylamino and isomers thereof.

Alkoxyalkylamino means methoxypropylamino, methoxyethylamino, ethoxyethylamino, propoxyethylamino and isomers thereof.

The novel process can be represented schematically as follows:

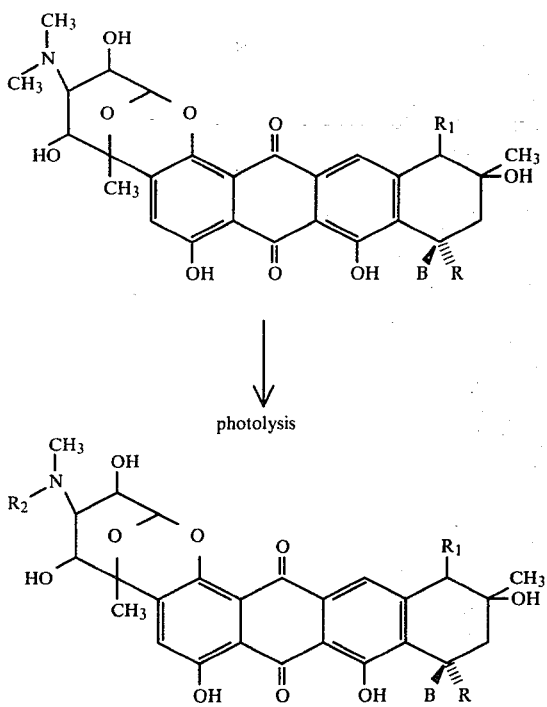

wherein R, $R_1$, $R_2$, and B are the same as defined above.

The process involves subjecting the compound of formula II to photolysis in the presence of a solvent to provide the compound of formula I. The photolysis is accomplished by exposure to either sunlight or ultraviolet light for a period of time of about 2 to 240 hours, at a temperature of about 0° to 40° C. The preferred exposure temperature is 20° C. to 30° C. Suitable solvents include chloroform, methanol, ethyl acetate, methylenechloride, tetrahydrofuran, or mixtures thereof. The preferred solvent is a mixture of chloroform and methanol in a ratio of 9:1.

Many of the compounds that can be used in the process of this invention are known in the art and have been published in the literature. For example, nogalamycin, nogalarol, nogalarene, nogalamycinic acid, nogamycin, 7-O-alkylnogarols and 7-deoxynogarols. Also con-nogamycin, con-7-nogarols and con-deoxynogarols are described and claimed in Applicant's pending application Ser. No. 060,326, filed July 25, 1979, now abandoned. The essential material constituting a disclosure of how to prepare con-nogamycin, con-7-nogarols and con-7-deoxynogarols is incorporated here by reference from patent application Ser. No. 060,326, filed July 25, 1979.

The novel N-demethyl compounds of this invention may be recovered by methods well known in the art such as crystallization, evaporation, precipitation, extraction, and combinations thereof. The compounds are unstable during chromatography so that method of purifying them is difficult. However, the compounds can be converted to their N-acyl derivatives and the derivatives purified and characterized by use of chromatography.

The novel compounds of the present invention can be acylated at one or more of the available hydroxyl groups under standard acylating conditions with an appropriate acid halide or anhydride to give the acylated compound.

The acylation is carried out in the presence of an acid-binding agent. Suitable acid-binding agents include: amines such as pyridine, quinoline, and isoquinoline, and buffer salts such as sodium acetate. The preferred base is pyridine. Carboxylic acids suitable for acylation include (a) saturated or unsaturated, straight or branched chain aliphatic carboxylic acids, for example, acetic, propionic, butyric, isobutyric, tertbutylacetic, valeric, isovaleric, caproic, caprylic, decanoic, dodecanoic, lauric, tridecanoic, myristic, pentadecanoic, palmitic, margaric, stearic, acrylic, crotonic, undecylenic, oleic, hexynoic, heptynoic, octynoic acids, and the like; (b) saturated or unsaturated, alicyclic carboxylic acids, for example, cyclobutanecarboxylic acid, cyclopentanecarboxylic acid, cyclopentenecarboxylic acid, methylcyclopentenecarboxylic acid, cyclohexanecarboxylic acid, dimethylcyclohexanecarboxylic acid, dipropylcyclohexanecarboxylic acid, and the like; (c) saturated or unsaturated, alicyclic aliphatic carboxylic acids, for example, cyclopentaneacetic acid, cyclopentanepropionic acid, cyclohexaneacetic acid, cyclohexanebutyric acid, methylcyclohexaneacetic acid, and the like; (d) aromatic carboxylic acids, for example, benzoic acid, toluic acid, naphthoic acid, ethylbenzoic acid, isobutylbenzoic acid, methylbutyl benzoic acid, and the like; and (e) aromatic aliphatic carboxylic acids, for example, phenylacetic acid, phenylpropionic acid, phenylvaleric acid, cinnamic acid, phenylpropiolic acid, and naphthylacetic acid, and the like. Also, suitable halo-, nitro-, amino-, cyano-, and lower alkoxyhydrocarbon carboxylic acids include hydrocarboncarboxylic acids as given above which are substituted by one or more of halogen, nitro, amino, cyano, or lower alkoxy, advantageously lower alkoxy of not more than six carbon atoms, for example, methoxy, ethoxy, propoxy, butoxy, amyloxy, hexyloxy groups and isomeric forms thereof. Examples of such substituted hydrocarbon carboxylic acids are:

mono-, di- and trichloroacetic acid;
α- and β-chloropropionic acid;
α- and γ-bromobutyric acid;
α- and δ-iodovaleric acid;
mevalonic acid;
2- and 4-chlorocyclohexanecarboxylic acid;
shikimic acid;
2-nitro-1-methyl-cyclobutanecarboxylic acid;
1,2,3,4,5,6-hexachlorocyclohexanecarboxylic acid;
3-bromo-2-methylcyclohexanecarboxylic acid;
4- and 5-bromo-2-methylcyclohexanecarboxylic acid;
5- and 6-bromo-2-methylcyclohexanecarboxylic acid;
2,3-dibromo-2-methylcyclohexanecarboxylic acid;
2,5-dibromo-2-methylcyclohexanecarboxylic acid;
4,5-dibromo-2-methylcyclohexanecarboxylic acid;
5,6-dibromo-2-methylcyclohexanecarboxylic acid;
3-bromo-3-methylcyclohexanecarboxylic acid;
6-bromo-3-methylcyclohexanecarboxylic acid;
1,6-dibromo-3-methylcyclohexanecarboxylic acid;
2-bromo-4-methylcyclohexanecarboxylic acid;
1,2-dibromo-4-methylcyclohexanecarboxylic acid;
3-bromo-2,2,3-trimethylcyclopentanecarboxylic acid;
1-bromo-3,5-dimethylcyclohexanecarboxylic acid;
homogentisic acid, o-, m-, and p-chlorobenzoic acid;
anisic acid;
veratric acid;
trimethoxybenzoic acid;
trimethoxycinnamic acid;
4,4'-dichlorobenzilic acid;
o-, m-, and p-nitrobenzoic acid;
cyanoacetic acid;

3,4- and 3,5-dinitrobenzoic acid;
2,4,6-trinitrobenzoic acid;
cyanopropionic acid;
ethoxyformic acid (ethyl hydrogen carbonate);
and the like.

Acid addition salts of the compounds of Formula I wherein $R_1$ is hydrogen or carbomethoxy and $R_2$ is hydrogen can be made by neutralizing the compound with an appropriate acid to below about pH 7.0, and advantageously to about pH 2 to pH 6. Suitable acids for this purpose include tartaric, glucuronic, and lactic which give water soluble salts, and hydrochloric, sulfuric, phosphoric, sulfamic, hydrobromic, and the like which give relatively water insoluble salts.

Compounds of Formula I wherein $R_1$ is carboxy form salts with nontoxic alkali metals and alkaline earth metals. Metal salts can be prepared by dissolving nogalamycinic acid in methanol, adding a dilute metal base until the pH of the solution is about 9 to 11, and freeze drying the solution to provide a dried residue consisting of the metal salt. Metal salts can be, for example, the sodium, potassium, and calcium salts. The salts can be used for the same antibacterial purposes as the free acid.

The novel compounds of the invention, acylates, acid addition salts thereof and metal salts inhibit the growth of microorganisms in various environments. For example, these compounds can be used for treating breeding places of silkworms, to prevent or minimize infections which are well known to be caused by *Bacillus sublilis.* Also the compounds are used to minimize or prevent odor in fish and fish crates caused by contamination with *B. subtilis.* Further, the compounds can be used to treat birds infected with *Mycobacterium avium.*

The compounds, acylates, acid addition and metal salts described herein are used in the treatment of mammals, including man. For example, the compounds inhibit the growth of *Streptococcus pyogenes* known to cause infection in man.

The acylated compounds described above can be given to an animal possessing the necessary enzyme to remove the acyl group, thus freeing the parent antibiotic compound which then inhibits susceptible bacteria.

The compounds of the present invention are presented for administration to humans and animals in unit dosage forms, such as sterile parenteral solutions or suspensions, containing suitable quantities of the compound of Formula I acylates, acid addition and metal salts thereof. Unit dosage forms may also be as tablets, capsules, pills, powders, granules, oral solutions or suspensions, and water-in-oil emulsions containing suitable quantities of compounds.

Dosage forms of the compound as discussed hereinafter refers to compounds of Formula I, acylates acid addition and metal salts thereof.

For oral administration, either solid or fluid unit dosage forms can be prepared. For preparing solid compositions such as tablets, the unit dosage is mixed with conventional ingredients such as talc, magnesium stearate dicalcium phosphate, magnesium aluminum silicate, calcium sulfate, starch, lactose, acacia, methylcellulose, and functionally similar materials as pharmaceutical diluents or carriers. Capsules are prepared by mixing the compound with an inert pharmaceutical diluent and filling the mixture into a hard gelatin capsule of appropriate size. Soft gelatin capsules are prepared by machine encapsulation of a slurry of the compound with an acceptable vegetable oil, light liquid petrolatum or other inert oil.

Fluid unit dosage forms for oral administration such as syrups, elixirs, and suspensions can be prepared. The water-soluble forms can be dissolved in an aqueous vehicle together with sugar, aromatic flavoring agents and preservatives to form a syrup. An elixir is prepared by using a hydroalcoholic (ethanol) vehicle with suitable sweeteners such as sugar and saccharin together with an aromatic flavoring agent.

Suspensions can be prepared with an aqueous vehicle with the aid of a suspending agent such as acacia, tragacanth, methylcellulose and the like.

For parenteral administration, which is preferred, fluid unit dosage forms are prepared utilizing the compound and a sterile vehicle, water being preferred. The compound, depending on the vehicle and concentration used, can be either suspended or dissolved in the vehicle. In preparing solutions the compound can be dissolved in water for injection and filter sterilized before filling into a suitable vial or ampoule and sealing. Advantageously, adjuvants such as a local anesthetic, preservative and buffering agents can be dissolved in the vehicle. To enhance the stability, the compositions can be frozen after filling into the vial and the water removed under vacuum. The dry lyophilized powder is then sealed in the vial and an accompanying vial of water for injection is supplied to reconstitute the liquid prior to use. Parenteral suspensions can be prepared in substantially the same manner except that the compound is suspended in the vehicle instead of being dissolved and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

The term "unit dosage form", as used in the specification, refers to physically discrete units suitable as unitary dosages for human subjects and animals, each unit containing a predetermined quantity of active material calculated to produce the desired therapeutic effect in association with the required pharmaceutical diluent, carrier or vehicle. The specifications for the novel unit dosage forms of this invention are dictated by and directly dependent on (a) the unique characteristics of the active material and the particular effect to be achieved and (b) the limitations inherent in the art of compounding such an active material for use in humans and animals, as disclosed in detail in this specification, these being features of the present invention. Examples of suitable unit dosage forms in accord with this invention are ampoules and vials, segregated multiples of the foregoing, and other forms as herein described.

An effective quantity of the compound is employed in treatment. The dosage of the compound for treatment depends on many factors that are well known to those skilled in the art. They include, for example, the route of administration and the potency of the particular compound. A dosage schedule for humans of from about 500 to about 5000 mg. of compound in a single dose, administered parenterally are effective for treating bacterial infections. When initial dosages at the lower end of the above range are employed, the mammal's progress is monitored and dosages on subsequent days are increased in the event that the patient or animal response is deemed by the attending physician or veterinarian to be absent or insufficient. The systemic toxicity of compounds of this invention must be carefully evaluated and subsequent dosages determined by evaluating the benefits of the drug in relationship to any such toxic manifestations.

The following examples are illustrative of the process and products of the invention, but are not to be construed as limiting. All percentages are by weight and all solvent mixture proportions are by volume unless otherwise noted. All temperatures are in degrees Centigrade.

EXAMPLE 1

N-Demethylnogalamycin and hydrochloride salt thereof

One gram of nogalamycin is dissolved in 500 ml. of chloroform. The solution is allowed to stand exposed to outside light for 4 days. The solution is extracted with three 50-ml. portions of 0.1 N HCl. The combined extracts are adjusted to pH 7.8 with 1 N sodium hydroxide and extracted with three 50-ml. portions of chloroform. The combined chloroform extracts are dried over magnesium sulfate, filtered, and evaporated to dryness in vacuo—yield 618 mg. of N-demethylnogalamycin. TLC in acetone-methanol-water (80:18:2) shows the strongest spot for N-demethylnogalamycin, $R_f$ 0.22. There are two weaker spots, one of which moves with nogalamycin. UV (EtOH) 208 nm ($\epsilon$18,500), 236 nm ($\epsilon$46,750), 219 nm ($\epsilon$23,000), 292 nm ($\epsilon$8,540), 478 nm ($\epsilon$14,040); IR (nujol) 3320, 1715, 1645, 1610, 1560, 1275, 1215, 1135, 1080, 1035, 995, 915, 750 710 cm$^-$.

EXAMPLE 2

N-acetyl-N-demethylnogamycin

Eight hundred mg of N-demethylnogalamycin is dissolved in a mixture of 10 ml of methanol and 2 ml of acetic anhydride. After the solution has stood at room temperature for 4 hours, it is evaporated to dryness under reduced pressure. The residue is chromatographed on 90 g of silica gel using chloroform-methanol (19:1) and collecting 201 five-ml fractions. Fractions 100-201 are combined and evaporated to dryness in vacuo to give 470 mg of N-acetyl-N-demethylnogalamycin; homogenous by TLC, Rf 0.38 in CHCl$_3$—CH$_3$OH (9:1); $[\alpha]_D$+485°; (c 0.286, CHCl$_3$); UV (EtOH) 236 nm ($\epsilon$38,400), 258 nm ($\epsilon$19,200), 290$_{sh}$ nm ($\epsilon$12,800); IR (Nujol) 3380, 1715, 1705, 1650, 1615, 1585, 1285, 1215, 1135, 1100, 1045, 1025, 1000, 915, 875, 820, 750 cm$^{-1}$; $^1$H NMR (CDCl$_3$) $\delta$1.1-1.7 (m, 12H), 2.10 (s, 3H), 3.20 (s, 3H), 3.25, 3.53, 3.62, 3.68 (4s, 12H), 2.8-4.62 (m), 5.22, 5.55, 5.88 (3 broad s, 3H), 7.26 (s, 1H), 7.52 (s, 1H), $^{13}$C NMR (CDCl$_3$) $\delta$191.1, 179.8, 174.7, 171.6, 161.6, 155.8, 146.9, 143.8, 136.5, 133.5, 130.4, 125.2, 116.1, 114.2, 113.9, 100.7, 95.62, 84.3, 81.0, 77.8, 75.7, 74.0, 71.5, 69.4, 67.3, 61.1, 59.2, 58.7, 56.8, 52.2, 48.5, 40.0, 32.2, 29.4, 23.6, 22.4, 18.0, 14.6; mass spectrum m/e 815.

EXAMPLE 3

N-Demethyldisnogamycin

One gram of disnogamycin is dissolved in 500 ml of chloroform-methanol (9:1), and the solution is exposed to outdoor light for 3 days. The solution is then evaporated in vacuo to give 1.03 g. This material is chromatographed on 50 g of silica gel using chloroform-methanol (9:1) for 118 five-ml fractions. A further 147 fractions are collected eluting with chloroform-methanol (82.5:17.5). Fractions 175-257 are pooled and evaporated in vacuo to give 267 mg of N-demethyldisnogamycin. TLC (CHCl$_3$—CH$_3$OH-H$_2$O; 78:20:2) gave a strong spot, R$_f$0.39, and two very weak less polar spots; $[\alpha]_D$+328° (c 0.186, CHCl$_3$); UV (EtOH) 235 nm ($\epsilon$42,200), 258 nm ($\epsilon$21,660), 293 nm ($\epsilon$8,800), 473 nm ($\epsilon$14,950); IR (Nujol) 3310, 1660, 1020, 1585, 1290, 1225, 1110, 1050, 1035, 1005, 915, 890, 850, 830, 775, 755 cm$^{-1}$; $^1$H NMR (DMSO) $\delta$1.08, 1.29, 1.59, (m, 12H), 2.36 (s, 3H), 3.07, 3.39, 3.41 (3s, 9H), 2.08-4.0 (m), 4.88 (m, 1H), 5.24 (broad s, 1H), 5.55 (d, 1H), 7.10 (s, 1H), 7.37 (s, 1H); $^{13}$C NMR (DMSO) $\delta$191.4, 179.2, 160.8, 154.6, 147.4, 146.0, 137.0, 133.3, 129.5, 124.0, 119.6, 116.4, 114.6, 113.2, 99.9, 95.7, 84.2, 80.3, 77.5, 75.2, 74.5, 72.8, 72.0, 71.8, 67.1, 66.5, 60.8, 57.6, 48.1, 44.7, 43.4, 33.8, 28.6, 23.5, 18.0, 14.6; mass spectrum m/e 715.

EXAMPLE 4

7-Con-O-methyl-N-demethylnogarol

A solution of 1.98 g of 7-con-O-methylnogarol in 1 liter of chloroform-methanol (9:1) is allowed to stand exposed to outside light for 13 days. The solution is evaporated to dryness in vacuo. The residue is dissolved in 200 ml of chloroform, and the solution is extracted with three 100-ml portions of 0.1 N hydrochloric acid. The combined extracts are adjusted to pH 7.7 with 1 N sodium hydroxide solution and extracted with three 100-ml portions of chloroform. The combined extracts are dried over magnesium sulfate, filtered, and evaporated in vacuo to give 1.004 g of residue. This material is chromatographed on 50 g of silica gel eluting with chloroform-methanol (9:1) for sixty 10-ml fractions then 82.5:17.5 for 176 fractions. The fractions are pooled on the basis of TLC in chloroform-methanol-water (78:20:2). The most polar material is in fractions 134-256 which were combined and evaporated in vacuo. The yield of 7-con-O-methyl-N-demethylnogarol is 476 mg.

TLC in the above solvent gives a strong spot, R$_f$0.17, and two weak spots one of which is starting material; UV (EtOH) 234.5 nm ($\epsilon$40,750), 259 nm ($\epsilon$20,500), 288$_{sh}$ ($\epsilon$12,950), IR (Nujol) 3420, 1665, 1620, 1575, 1330, 1270, 1230, 1110, 1075, 1015, 940, 925, 880, 855, 835, 785, 760 cm$^{-1}$; $^{13}$C NMR (CDCl$_3$) $\delta$190.5, 179.9, 161.3, 155.5, 147.9, 146.6, 137.4, 132.5, 129.5, 125.6, 120.5, 115.9, 114.0, 112.4, 96.8, 75.1, 74.6, 73.1, 72.8, 68.0, 67.5, 57.8, 44.3, 44.0, 35.9, 30.1, 23.6.

EXAMPLE 5

7-Con-O-methyl-N-acetyl-N-demethylnogarol

One hundred mg of 7-con-O-methyl-N-demethylnogarol is dissolved in a mixture of 1.5 ml of methanol and 0.3 ml of acetic anhydride. The solution is allowed to stand at room temperature for 4 hours. The solution is evaporated to dryness in vacuo, and the residue is chromatographed on 20 g of silica gel using chloroform-methanol (95:5) and collecting 110 five-ml fractions. On the basis of TLC in chloroform-methanol (9:1), fractions 25-35 are combined and evaporated in vacuo, yield 20 mg of 7-con-O-methyl-N-acetyl-N-demethylnogarol, R$_f$ 0.22 in the above solvent; $^1$H NMR (DMSO) $\delta$1.21 (s, 3H), 1.64 (s, 3H), 2.48 (s, 3H), 3.30 (s, 3H), 3.42 (s, 3H), 5.98 (d, 1H), 7.12 (s, 1H), 7.17 (s, 1H); $^{13}$C NMR (DMSO) 191.4, 179.5, 171.1, 160.7, 154.7, 146.9, 146.6, 136.5, 133.4, 129.1, 124.5, 119.7, 116.6, 114.9, 113.0, 96.0, 75.7, 71.3, 68.4, 67.6, 61.1, 57.1, 44.5, 37.9, 29.6, 25.8, 23.8, 21.7.

EXAMPLE 6

Utilizing procedures similar to those of Examples 1, 3 and 4 but substituting the appropriate nogalamycin analog for nogalamycin, there are obtained:
N-demethylnogalamycinic acid,
N-demethyl-7-deoxynogalarol,
7-O-ethyl-N-demethylnogarol,
7-O-propyl-N-demethylnogarol,
7-O-isopropyl-N-demethylnogarol,
7-O-n-butyl-N-demethylnogarol,
7-O-isobutyl-N-demethylnogarol,
7-O-tertiarybutyl-N-demethylnogarol,
con-7-aminoethyl-N-demethyl-deoxynogarol
con 7-amino-n-propyl-N-demethyl-7-deoxynogarol,
con 7-amino-isopropyl-N-demethyl-7-deoxynogarol,
con 7-amino-n-butyl-N-demethyl-7-deoxynogarol,
con 7-amino-isobutyl-N-demethyl-7-deoxynogarol,
con 7-aminotertbutyl-N-demethyl-7-deoxynogarol,
con 7-ethylthio-N-demethyl-7-deoxynogarol,
con 7-n-propylthio-N-demethyl-7-deoxynogarol,
con 7-isopropylthio-N-demethyl-7-deoxynogarol,
con 7-n-butylthio-N-demethyl-7-deoxynogarol,
con 7isobutylthio-N-demethyl-7-deoxynogarol,
con 7-tertiarybutylthio-N-demethyl-7-deoxynogarol,
con-7-O-n-propionyl-N-demethylnogarol,
con 7-O-n-butyryl-N-demethylnogarol,
con 7-O-isobutyryl-N-demethylnogarol,
con 7-O-n-tertiarybutyryl-N-demethylnogarol,
con 7-bis(carbo-n-propoxy)methyl-N-demethyl-7-deoxynogarol,
con 7-bis(carboisopropoxy)methyl-N-demethyl-7-deoxynogarol,
con 7-bis(carbo-n-butoxy)methyl-N-demethyl-7-deoxynogarol,
con 7-bis(carboisobutoxy)methyl-N-demethyl-7-deoxynogarol,
con 7-bis(carbotertiarybutoxy)methyl-N-demethyl-7-deoxynogarol,
con 7-methoxypropylamino-N-demethyl-7-deoxynogarol,
con 7-methoxyisopropylamino-N-demethyl-7-deoxynogarol,
con 7-ethoxyethylamino-N-demethyl-7-deoxynogarol,
con 7-propoxyethylamino-N-demethyl-7-deoxynogarol,
con 7-isopropoxyethylamino-N-demethyl-7-deoxynogarol,
con 7-amino-N-demethyl-7-deoxynogarol,
con 7-propylamino-N-demethyl-7-deoxynogarol,
con 7-isopropylamino-N-demethyl-7-deoxynogarol,
con 7-n-butylamino-N-demethyl-7-deoxynogarol,
con 7-isobutylamino-N-demethyl-7-deoxynogarol,
con 7-tertiarybutylamino-N-demethyl-7-deoxynogarol.

EXAMPLE 7

Utilizing procedures similar to those of Examples 2 and 5 but substituting the appropriate N-demethyl analog for N-demethylnogalamycin and 7-con-O-methyl-N-demethylnogarol there is obtained N-acetyl derivatives of N-demethyldisnogamycin and the N-methylnogalamycin analogs of the compounds of Example 6.

I claim:

1. A process for preparing a compound having the structure:

wherein R is selected from the group consisting of hydrogen and methoxy; $R_1$ is selected from the group consisting of hydrogen, carbomethoxy and carboxy; and B is selected from the group consisting of hydrogen and a nucleophile, which comprises subjecting a compound having the formula:

to photolysis, wherein R, and $R_1$ and B are the same as above.

2. A process according to claim 1 wherein the compound prepared is N-demethylnogalamycin.

3. A process according to claim 1 wherein the compound prepared is N-demethyldisnogamycin.

4. A process according to claim 1 wherein the compound prepared is 7-con-O-methyl-N-demethylnogarol.

5. A process according to claims 2, 3, 4 or 1, wherein the compound prepared is reacted with an acylating agent to form acylates thereof.

6. A process according to claim 1 wherein $R_1$ is hydrogen or carbomethoxy.

7. A process according to claims 2, 3, 4 or 6 wherein the compound prepared is neutralized with an acid to form biologically-acceptable addition salts thereof.

8. A process according to claim 1 wherein $R_1$ is carboxy.

9. A process according to claim 7 wherein the compound prepared is reacted with a metal base selected from the group consisting of non-toxic alkali and alkaline earth metal bases to form non-toxic metal salts thereof.

* * * * *